United States Patent [19]

Palermo

[11] Patent Number: 4,886,067

[45] Date of Patent: Dec. 12, 1989

[54] STEERABLE GUIDEWIRE WITH SOFT ADJUSTABLE TIP

[75] Inventor: Thomas J. Palermo, Methuen, Mass.

[73] Assignee: C. R. Bard, Inc., Murray Hill, N.J.

[21] Appl. No.: 292,934

[22] Filed: Jan. 3, 1989

[51] Int. Cl.⁴ .............................................. A61B 6/00
[52] U.S. Cl. ................................. 128/657; 128/772; 604/164; 604/280
[58] Field of Search ................. 128/657, 772; 604/95, 604/164, 170, 280, 282

[56] References Cited

U.S. PATENT DOCUMENTS

| | | | |
|---|---|---|---|
| 2,574,840 | 11/1951 | Pieri et al. | 604/95 |
| 3,060,972 | 10/1962 | Sheldon | 128/772 |
| 3,452,740 | 7/1969 | Muller | 128/772 |
| 3,503,385 | 3/1970 | Stevens | 128/657 |
| 3,521,620 | 7/1970 | Cook | 604/170 |
| 3,528,406 | 9/1970 | Jeckel et al. | 128/772 |
| 3,547,103 | 12/1970 | Cook | 128/772 |
| 3,552,384 | 1/1971 | Pierie et al. | 128/657 |
| 3,625,200 | 12/1971 | Muller | 128/772 |
| 3,749,086 | 7/1973 | Kline et al. | 128/772 |
| 3,773,034 | 11/1973 | Burns et al. | 128/657 |
| 3,906,938 | 9/1975 | Fleischhacker | 128/772 |
| 4,003,369 | 1/1977 | Heilman | 128/772 |
| 4,033,331 | 7/1977 | Guss et al. | 128/657 |
| 4,080,706 | 3/1978 | Heilman et al. | 128/772 |
| 4,215,703 | 8/1980 | Willson | 128/772 |
| 4,245,624 | 1/1981 | Komiya | 128/772 |
| 4,474,174 | 10/1984 | Petruzzi | 128/772 |
| 4,548,206 | 10/1985 | Osborne | 128/772 |
| 4,719,924 | 1/1988 | Crittenden et al. | 128/772 |
| 4,721,117 | 1/1988 | Mar et al. | 128/772 |

Primary Examiner—Max Hindenburg
Assistant Examiner—Randy Citrin
Attorney, Agent, or Firm—Wolf, Greenfield & Sacks

[57] ABSTRACT

A steerable guidewire for guiding a catheter includes an elongate hollow shaft having a distal core wire mounted at its distal end. The distal core wire tapers in a distal direction and has a flexible distral tip. The core wire is received within a helical coil mounted to the distal end of the guidewire, the distal tip of the core wire being attached to the distal tip of the helical coil. A pull wire extends the length of the guidewire through the hollow shaft and the helical coil and is connected, eccentrically, to the distal tip of the helical coil by a small diameter internal spring, the proximal end of which is attached to the distal end of the pull wire and the distal end of which is attached to the distal end of the helical coil. Pulling on the pull wire causes the distal tip of the guidewire to assume a curved configutation. The resilience of the internal spring, however, permits the distal tip of the guidewire to assume a more straightened configuration even while the pull wire is tensioned whereby the distal tip of the guidewire may yield to conform to irregularities in a patient's vasculature.

5 Claims, 3 Drawing Sheets

STEERABLE GUIDEWIRE WITH SOFT ADJUSTABLE TIP

FIELD OF THE INVENTION

This invention relates to guidewires used in the placement of catheters in cardiovascular surgical procedures and, particularly, to improvements in small diameter steerable guidewires.

BACKGROUND OF THE INVENTION

This invention relates to a steerable guidewire having an adjustable J-shaped distal tip that is adapted for use in small bore blood vessels such as the coronary arteries. Such guidewires typically are involved in percutaneous transluminal coronary angioplasty procedures. More particularly, the present invention concerns an improvement to the invention described in U.S. Pat. No. 4,719,924. That patent discloses a small diameter steerable guidewire having an adjustable flexible helical coil tip in which a pull wire extends the length of the guidewire, from its proximal to the distal tip of the coil. The distal tip of the guidewire normally assumes a generally straight configuration but can be altered to a J-shaped configuration upon tensioning of the pull wire. The degree of curvature of the distal tip is dependent on the extent to which the pull wire is tensioned.

Although the device described in U.S. Pat. No. 4,719,924 is highly effective in changing the curvature of the distal tip of the guidewire while the guidewire is in the patient's blood vessel, there are some instances in which it would be desirable for the distal tip of the guidewire to be more flexible so as to be able better to follow the contours and unanticipated tortuous configurations of the patient's blood vessel. When the pull wire is tensioned to cause the distal tip of the guidewire to assume a curved configuration, the tension on the pull wire tends to stiffen somewhat and retain the distal tip of the guidewire in that curved configuration and presents resistance to bending of the distal tip of the helical coil to a more straightened or altered curved configuration in order to follow the irregularities of the patient's blood vessel. Accordingly, there is a need for a small diameter steerable guidewire in which the curved configuration of the distal end of the guidewire can be adjusted from the proximal end of the guidewire while the guidewire is disposed within a patient's blood vessel yet which permits flexure of the curved distal end of the guidewire to a more straight or altered curved configuration in order to follow the contours of the patient's blood vessel. It is among the general objects of the invention to provide such a guidewire.

SUMMARY OF THE INVENTION

The guidewire includes an elongate torsionally rigid shaft formed from a solid walled tube. A slot is formed in the distal end of the tube and a relatively short core wire is attached to and extends distally from the distal end of the tube. The core wire is attached so as to leave a portion of the slot unobstructed. A helically wound outer spring is connected to and encloses the distal region of the tube and all of the core wire. The core wire, which is circular in cross-section throughout most of its length, has a distal portion that is flattened progressively toward its distal tip, the distal tip being attached to the distal tip of the helical coil at a rounded tip weld. The pull wire extends through the full length of the guidewire. The distal tip of the pull wire terminates short of the distal tip of the helical coil and is connected to the tip of the helical coil by a small diameter spring formed from small diameter wire. The pull wire extends proximally between the core wire and the outer helical coil, through the opening in the tube, and then through the tube, exiting at the proximal end of the tube. By varying the tension on the pull wire, the degree of curvature at the distal end of the guidewire can be varied controllably. Because the tip of the pull wire is connected to the tip of the outer coil by the small diameter extendable helical spring, the distal tip of the helical coil remains flexible, even though it is drawn into a J-curve. The flexibility of the small spring is such as to permit the distal tip of the wire to straighten out or assume an altered curvature in order to follow the contours of the blood vessel.

A tip adjustment mechanism is provided to control the longitudinal position of the pull wire.

It is among the general objects of the invention to provide an improved small diameter steerable guidewire having an adjustable curvature tip in which the tip may yield and flex from its curved configuration.

Another object of the invention is to provide a small diameter steerable guidewire having an adjustable curvature tip which incorporates a pull wire and in which the distal end of the pull wire is connected to the distal end of the guidewire by an extendable spring element.

Another object of the invention is to provide a small diameter steerable guidewire having an adjustable tip configuration which can straighten or assume an altered curvature in order to follow the contours of a patient's blood vessel even while the pull wire of the guidewire biases the tip in a curved configuration.

DESCRIPTION OF THE DRAWINGS

The foregoing and other objects and advantages of the invention will be appreciated more fully from the following further description thereof, with reference to the accompanying drawings wherein.

DESCRIPTION OF THE ILLUSTRATIVE EMBODIMENT

Figure 1:
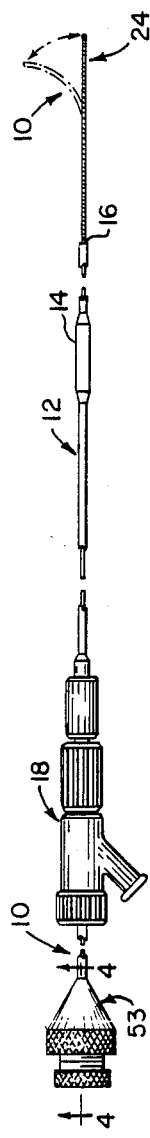
FIG. 1 is a fragmented side elevation of a catheter with the guidewire of the invention extending through the catheter.

FIG. 1 illustrates the guidewire 10 of the present invention in combination with a balloon dilatation catheter 12. The catheter 12 may be generally of the type described in U.S. Pat. No. 4,545,390 to Leary. The dilatation catheter 12, particular when intended for use in a small artery such as a coronary artery, is relatively slender and, for example, may have an outer diameter of the order of 0.050". The inner dimensions of its lumens, of course, are even smaller and its main lumen may be of the order of 0.022" diameter at its smallest cross sectional dimension. The catheter has a dilatation balloon 14 at its distal end and a central lumen which is used to deliver liquids such as radiopaque dyes or anticoagulants and also to make distal pressure measurements. The main lumen of the catheter 12 opens at an outlet 16 at the distal tip of the catheter. The catheter also is provided with an inflation lumen (not shown) which is smaller and communicates with the interior of the balloon 14 to inflate and deflate the balloon. The proximal end of the catheter may be provided with a Y-fitting 18 to provide communication at the proximal end of the catheter to each of the central and inflation lumens of the balloon dilatation catheter 12.

Figure 2:
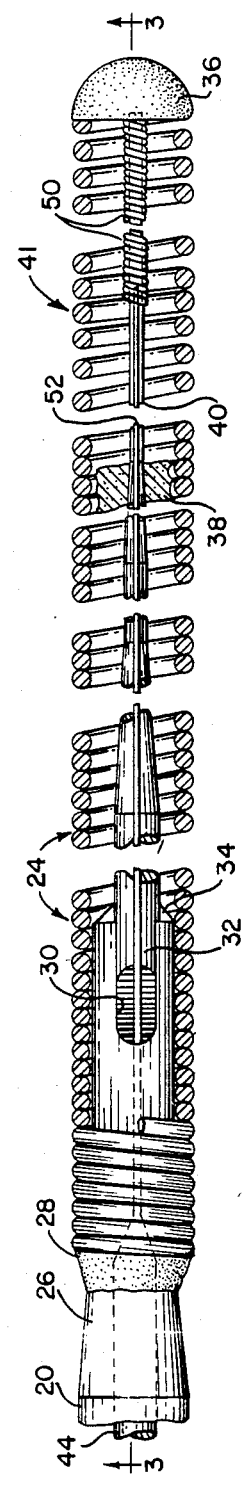
FIG. 2 is an enlarged, fragmented and broken away illustration of the distal region of the guidewire.
Figure 3:
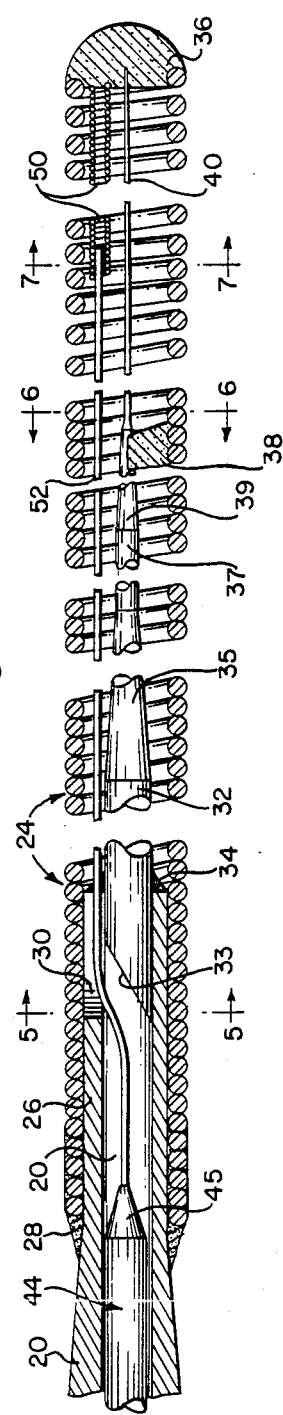
FIG. 3 is a sectional illustration of the guidewire as seen along the line 3—3 of FIG. 2.

As shown in FIGS. 1-3, the guidewire of the present invention includes an elongate main wire 20 which is hollow and is in the form of a solid walled tube having a central lumen 22. The main wire 20 may be formed from stainless steel hypodermic tubing. The main wire 20 extends along the major portion of the length of the guidewire. By way of example, in a guidewire having an overall length of about 180 cm, the main wire 20 may have a length of about 150 cm. When the guidewire is used with a coronary angioplasty catheter, the main wire has an outer diameter not greater than about 0.020" and, in the illustrative embodiment of the invention, has a wall thickness of 0.003". The solid walled configuration of the main wire is sufficiently torsionally rigid to transmit substantially fully and smoothly to the distal end of the wire rotation applied at the proximal end. Thus, the distal end of the guidewire 10 can be caused to rotate in controlled increments to permit steering of the guidewire.

An elongate helical outer coil, indicated generally at 24 is attached to the distal end of the main wire 20. The spring 24 extends along a relatively short portion of the overall length of the guidewire 10. For example, a guidewire having an overall length of about 180 cm may have a spring 24 about 30 cm in length. In the preferred embodiment of the invention, the outer diameter of the spring 24 is not substantially greater than that of the main wire 20 and, preferably, is the same diameter as the main wire 20. The distal end of the main wire 20 is reduced in outer diameter as by grinding otherwise tapering the wire lengthwise so that it may fit within the proximal end of the spring 24 in a manner which enables the diameter of the spring 24 to remain substantially the same diameter as the main wire 20.

The proximal end of the spring 24 is connected to the tapered end of the main wire 20 by a brazed joint 28. The tapered distal end 26 of the main wire 20 is provided with a longitudinal slot 30 to permit passage of a pull wire, as will be described. The guide wire 10 also includes a relatively short distal core wire 32 which is secured to and extends distally from the distal end of the main wire 20. In the illustrative embodiment the core wire may be about 31 cm long and may have a diameter of about 0.008", the wire 32 being tapered in a distal direction. The proximal end of the core wire 32 is received in the opening at the distal end 26 of the main wire 20 and is secured thereto with a brazed joint 34. The proximal end of the distal core wire 32 preferably is beveled, to define an upwardly and distally inclined ramp as indicated in FIG. 3 at 33, and is connected so that it terminates short of the blind end of the slot 30 to maintain a portion of the slot 30 open. The bevel at the end 33 of the core wire 32 enables a substantial portion of the slot 30 to be maintained open while providing an increased area of support for the core wire 32 by the distal end 26 of the main wire 20.

A distal portion of the core wire 32, about 13 cm in the illustrative embodiment, is generally tapered in a distal direction. The tapered configuration provides a progressively increasing flexibilty along that portion of the guidewire. The tip of the distal core wire extends to and is secured to a hemispherical tip weld 36. The core wire 32 is secured to the outer coil 24 at a distal brazed joint 38. The tapered portion of the core wire 32 may be formed in a stepped taper configuration including a tapered portion 35, a cylindrical portion 37, another tapered portion 39 and a terminal flattened portion 40. The tapered portion 35 may begin about 15 cm from the proximal end of the core wire 32 and may be about 4 cm long. The cylindrical portion 37 may be 0.006" diameter and about 6 cm long. The tapered portion 39 and flattened portion 40 into which it merges extend over an aggregate length of about 7 cm and are formed initially so that the proximal 6 cm portion is tapered (to about 0.002") and the distal 1 cm is cylindrical, 0.001" diameter. The distal 3 cm of the tip, thus formed, then is dropped flattened to forge the distal 2.5 cm into a tapering flattened ribbon-like segment. The foregoing tip configuration assures that when the pull wire is tensioned, the tip will flex generally along a plane that lies perpendicular to the general plane of the flattened tip portion. Additionally, the flattened tip portion makes the tip soft and flexible but in a manner that does not impair the ability of the tip to rotate with the guidewire as the proximal portion of the guidewire is rotated.

In accordance with the invention, the configuration of the distal segment 41 of the helical coil 24 may be controlled to vary the extent to which it is bent or curved without requiring removal of the guidewire from the patient. For that purpose, a pull wire 44 is provided. The pull wire extends nearly the full length of the guidewire, extending fully through the hollow main wire 20, through the slot 30 and between the core wire 32 and the outer helical coil 24. The pull wire includes a proximal segment about 0.006" diameter that extends from the proximal end of the guidewire to a location just short of the longitudinal slot 30. The pull wire then is tapered at 45 and, from the end of the taper 45 to the distal tip of the pull wire, the pull wire is of a diameter of the order of 0.002". The distal tip of the distal segment 52 of the pull wire is approximately 2 cm short of the distal tip of the outer coil 24 and is attached to the tip weld 36 by a small diameter helical spring 50 welded at one end to the distal tip of the tip segment 52 of the pull wire 44 and at its other end to the tip weld 36. The inner spring 50 may be of the order of 1.75 cm long, may be formed from LTC wire (alloy of nickel, chromium and gold) of the order of 0.002" diameter into a coil approximately 0.008" diameter. The LTC alloy provides a spring with good resilience that is relatively easy to weld to the stainless steel components of the guidewire and which also provides a highly radiopaque portion visible under fluoroscopy. The distal segment of the guidewire normally tends to maintain a straight configuration but can be drawn to a curve of varying degree by pulling on the guidewire to the degree desired as suggested in FIG. 8.

Figure 8:
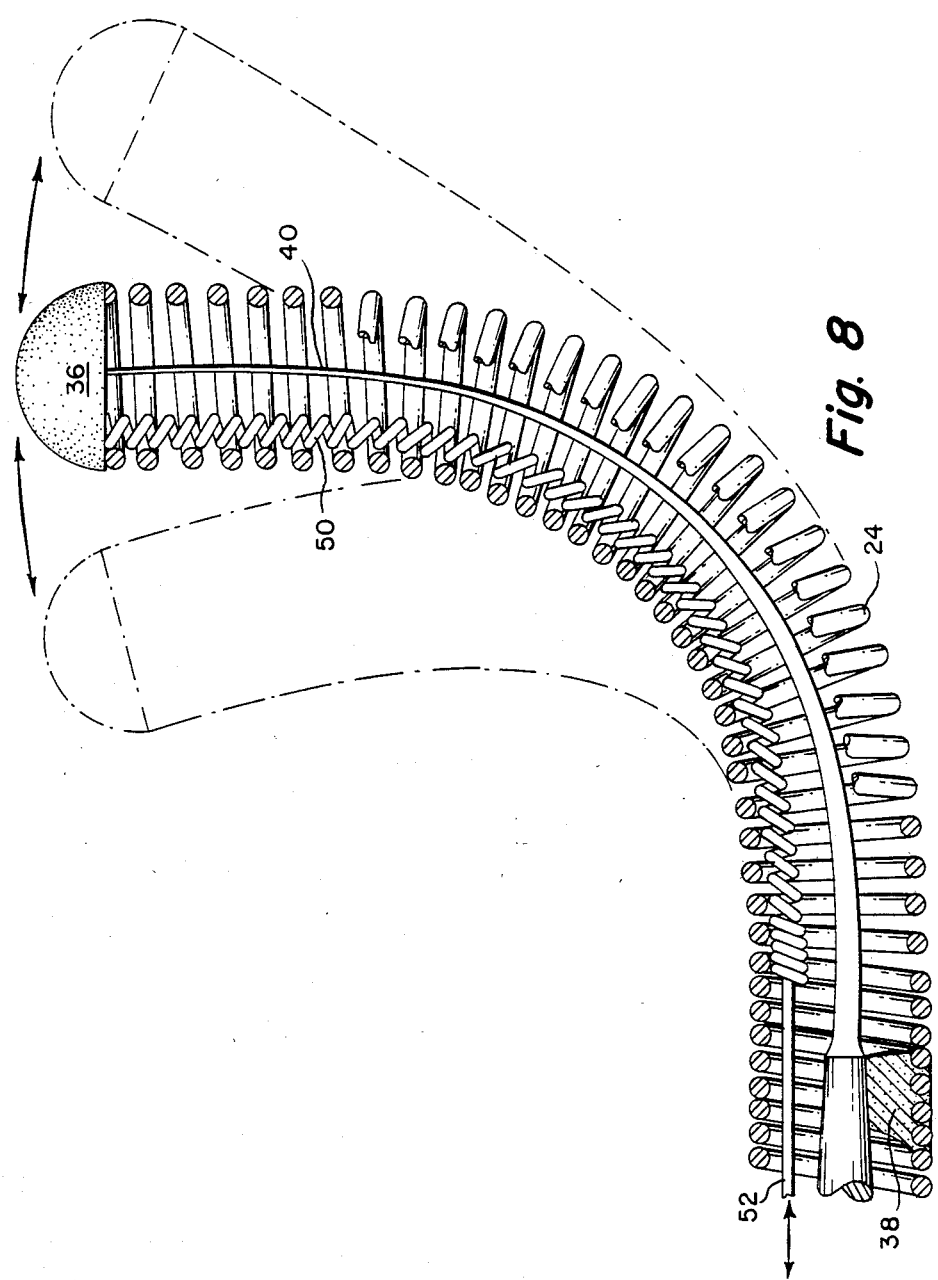
FIG. 8 is an illustration of the tip of the guidewire in a curved configuration.

FIG. 8 illustrates the configuration of the distal region of the guidewire when the pull wire is tensioned. When tensioned, the inner spring 50 will expand somewhat while at the same time the outer coil 24 will be drawn into a curved configuration to a degree dependent on the degree to which the pull wire is tensioned. It will be appreciated, that because the pull wire is not directly connected to the tip weld 36, but is connected through the inner spring 50, the distal segment of the outer coil 24 may flex to a straightened configuration even while the tension on the pull wire is maintained. Should such straightening or other change of curvature oppose the tension applied through the inner spring 50, the inner spring will yield and stretch as required in order to permit the outer coil 24 to assume the particular configuration. Thus, even though the distal tip of the guidewire may be drawn to a desired curve, the distal tip still is free to bend and follow the contours of the vascular anatomy of a patient, as required.

Figures 4, 5:
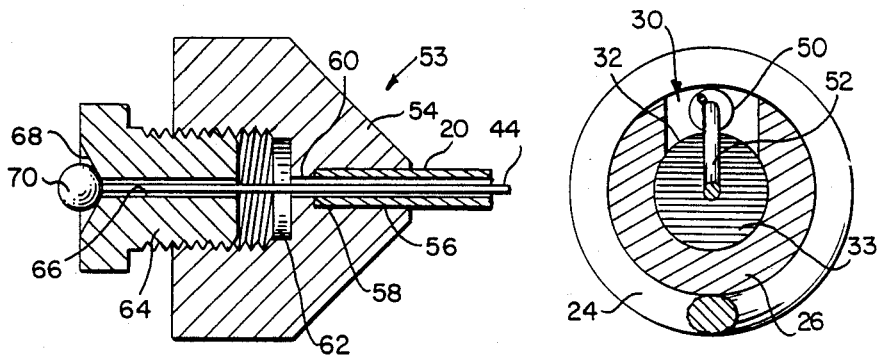
FIG. 4 is a sectional illustration of the tip adjustment mechanism as seen along the line 4—4 of FIG. 1.
FIG. 5 is a sectional illustration of the guidewire as seen along the line 5—5 of FIG. 3.
Figures 6, 7:
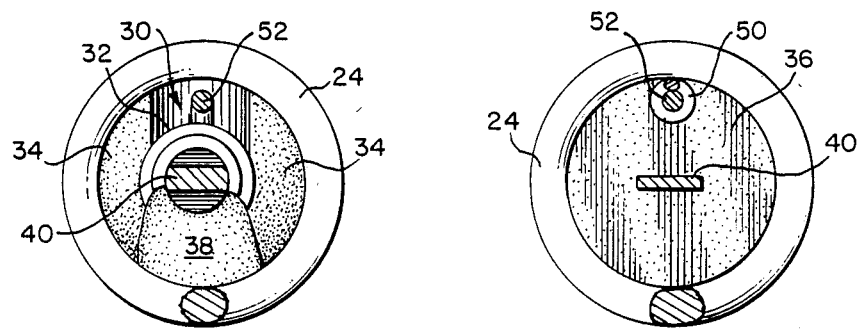
FIG. 6 is a sectional illustration of the guidewire as seen along the line 6—6 of FIG. 3.
FIG. 7 is a sectional illustration of the guidewire as seen along the line 7—7 of FIG. 3.

FIG. 4 shows, in enlarged detail, the tip adjustment mechanism, indicated generally by the reference character 53. The adjustment mechanism 53 includes a cap 54 having a socket 56 which fits over the proximal end of the main wire 20. Socket 56 terminates in a shoulder 58 which abuts the end of the wire 20. An opening 60 extends proximally from the socket 56 and opens into an enlarged internally threaded bore 62. An adjustment screw 64 is threaded into the bore 62. The adjustment screw 64 is provided with a central bore 66 which terminates in a conical depression 68 at the proximal end of the adjustment screw 64. The pull wire 44 thus may extend through the main wire 20, opening 60, bore 62 and bore 66 of the adjustment screw 64. An enlarged ball 70 or similar retention member is securely attached to the proximal end of the pull wire 44 and is seated within the depression 68. Rotation of the adjustment screw is effective to increase or decrease the pull on the pull wire 44. An increased pull on the pull wire draws the distal segment 38 of the guidewire to a curved configuration as suggested in FIG. 8, the extent of curve being dependent on the degree to which the pull wire 46 is pulled. The tip adjustment mechanism 52 may be manipulated to impart the desired degree of curvature to the distal segment 38 and may remain in that position until it is desired to change the curvature.

Thus, from the foregoing, it will be appreciated that the invention provides a small diameter steerable guidewire in which the curve at the distal tip may be controllably adjusted as desired from a straight configuration to a J configuration while the guidewire is in place in the patient and without requiring removal of the guidewire to adjust the tip. The flexibility of the curved distal tip, however, remains and it can assume a straightened or altered curved configuration in order to conform to the anatomy of the patient's vessel, as required. The distal tip of the guidewire and the connection between the pull wire and the distal tip of the helical coil are such as to permit yieldable movement between the two. The guidewire thus improves substantially the facility with which a dilatation procedure may be performed, particularly in small diameter blood vessels having tortuous passages such as the coronary arteries.

It should be understood, however, that the foregoing description of the invention is intended merely to be illustrative thereof and that other embodiments and modifications may be apparent to those skilled in the art without departing from its spirit.

Having thus described the invention, what I desire to claim and secure by letters patent is:

1. A steerable guidewire comprising:
   an elongate solid walled tubular main wire having a proximal and a distal end;
   an elongate helical coil having proximal and distal ends and being connected at its proximal end to the distal end of the main wire and extending distally of the main wire;
   a distal core wire having proximal and distal ends and being connected to and extending distally from the distal end of the main wire, the core wire extending through the lumen of the coil and having a distal tip connected to the distal tip of the coil at a rounded end cap;
   means defining a pull wire opening adjacent to the distal end of the main wire and adjacent the proximal end of the distal core wire;
   a pull wire having a proximal end and a distal end, the distal end of the pull wire terminating short of the distal tip of the helical coil;
   a longitudinally yieldable spring internal of the helical coil connecting the distal end of the pull wire with the distal end of the helical coil;
   the pull wire extending proximally between the core wire and the coil and through the opening into the lumen of the main wire, the pull wire extending proximally through the lumen of the main wire to the proximal end of the main wire;
   whereby the proximal end of the pull wire may be pulled to apply tension to the pull wire thereby to tension the internal spring and to draw at least a portion of the distal end of the helical coil into a curved configuration.

2. A steerable guidewire as defined in claim 1 wherein the outer diameter of the main wire is not greater than about 0.020".

3. A guidewire as defined in claims 1 or 2 wherein the core wire is tapered in a distal direction and in which the distal tip of the distal core wire is flat.

4. A guidewire as defined in claim 3 wherein the internal spring is disposed eccentrically in the helical coil and extends along the flat face of the flattened distal tip portion of the core wire.

5. A guidewire as defined in claim 4 wherein the distal end of the pull wire from a location proximally of the pull wire opening and extending to the connection thereof with the internal spring is reduced diameter.

* * * * *